(12) United States Patent
Rump et al.

(10) Patent No.: US 6,375,714 B1
(45) Date of Patent: Apr. 23, 2002

(54) DEVICE AND PROCESS TO PRODUCE ACTIVE OXYGEN IONS IN THE AIR FOR IMPROVED AIR QUALITY

(75) Inventors: Hanns Rump, Hausen; Olaf Kiesewetter, Geschwenda, both of (DE)

(73) Assignee: T.E.M.! Technishe Entwicklungen und Managament GmbH, Hausen (DE)

( * ) Notice: Subject to any disclaimer, the term of this patent is extended or adjusted under 35 U.S.C. 154(b) by 0 days.

(21) Appl. No.: 09/331,147

(22) PCT Filed: Dec. 11, 1997

(86) PCT No.: PCT/EP97/06925

§ 371 Date: Aug. 10, 1999

§ 102(e) Date: Aug. 10, 1999

(87) PCT Pub. No.: WO98/26482

PCT Pub. Date: Jun. 18, 1998

(30) Foreign Application Priority Data

Dec. 11, 1996 (DE) .......................................... 196 51 402

(51) Int. Cl.$^7$ ................................................. B03C 3/68
(52) U.S. Cl. .................... 95/3; 96/19; 96/96; 96/97; 361/235
(58) Field of Search ................. 96/18, 19, 97, 96/96; 95/2, 3, 8, 57; 361/226, 231, 233, 235; 323/903

(56) References Cited

U.S. PATENT DOCUMENTS

| | | | | |
|---|---|---|---|---|
| 3,641,740 A | * | 2/1972 | Schumann et al. ............ | 96/19 |
| 3,973,927 A | * | 8/1976 | Furchner et al. ................. | 95/3 |
| 4,284,417 A | * | 8/1981 | Reese et al. ...................... | 95/3 |
| 4,624,685 A | * | 11/1986 | Lueckenotte et al. ............ | 95/3 |
| 4,690,694 A | * | 9/1987 | Alig et al. ........................ | 95/3 |
| 4,901,194 A | | 2/1990 | Steinman et al. ....... | 361/235 X |
| 4,918,568 A | | 4/1990 | Stone et al. ................. | 361/231 |
| 5,695,549 A | * | 12/1997 | Feldman et al. ............ | 96/97 X |
| 5,759,487 A | * | 6/1998 | Jung ........................ | 96/19 X |

FOREIGN PATENT DOCUMENTS

| | | | | |
|---|---|---|---|---|
| CH | 600250 | | 6/1978 | |
| GB | 2304576 | | 3/1997 | |
| JP | 60185623 | | 9/1985 | |
| JP | 6304495 | * | 11/1994 | ..................... 96/19 |
| SU | 1012952 | * | 4/1983 | ..................... 96/19 |
| SU | 1018696 | * | 5/1983 | ..................... 96/19 |
| WO | 9322603 | | 11/1993 | |

OTHER PUBLICATIONS

Patent Abstract of Japan vol. 010, No. 029 (M–451) JP 60185623A Matsushita Denki Sangyokk, Sep. 21, 1985.

* cited by examiner

Primary Examiner—Richard L. Chiesa
(74) Attorney, Agent, or Firm—Horst M. Kasper

(57) ABSTRACT

The invention relates to a device for producing active oxygen ions in the air for improved air quality, comprising at least one air ionizer and an electric transformer producing sufficient electrical high voltage for air ionization. The air ionizer is coupled to a sensor which detects the oxidizable gas content in the air (air pollution sensor). On the basis of the detected content of such oxidizable gases, the electrical energy which is guided to the air ionizer is transformed by an electrical control device in such a way that only low-level ionization occurs at low concentration of oxidizable gases. Said ionization is sensor-controlled and can automatically be increased to a maximum value when the concentration of oxidizable gases rises.

28 Claims, 8 Drawing Sheets

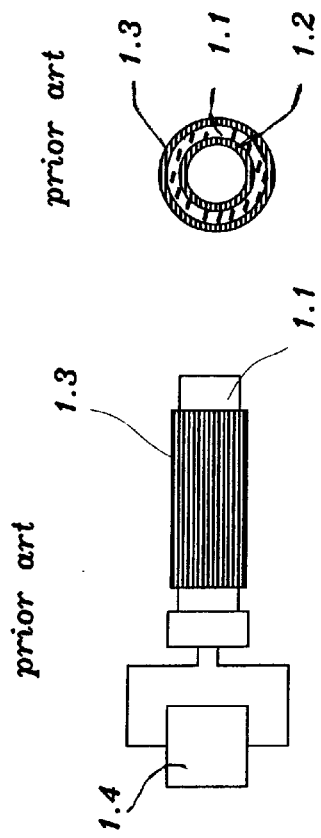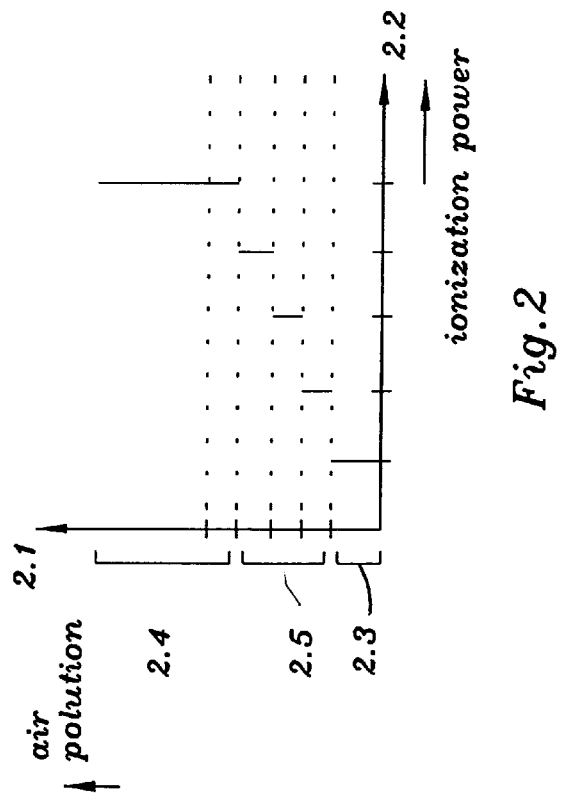

DEVICE AND PROCESS TO PRODUCE ACTIVE OXYGEN IONS IN THE AIR FOR IMPROVED AIR QUALITY

RELATED APPLICATIONS

This application is the national stage of International Application No. PCT/EP97/06925, filed on Dec. 11, 1997.

The invention relates to a device for generating active oxygen ions in the air for improving air, in particular breathing air, comprising at least one air ionizer and one electrical transformer generating a sufficient high voltage for air ionization.

Healthy breathing air is described as air without substantial parts of noxious gases or noticeable, in many cases unpleasant odorous substances. Healthy inhaled air is to contain a number as low as possible of bacteria, viruses and other germs, which is very important, in particular when knowing the fact that annually more than 40,000 people become sick with fatal results in Germany by airborne infections, for example in hospitals, in restaurants, and in means of mass transport, as was determined by a scientific study of the Robert-Koch-institute (Bundesgesundheitsblatt Issue 7/96, Page 246). The cost of these nosocominal infections are estimated by the authors to be more than 3 billion German Marks. odorous materials drastically reduces the comfort, the condition and the capability to concentrate and thus the life quality of the exposed human being. It can be easily realized that for example the stink of kerosene and other engine exhaust gases renders impossible the tasting of delicious meals or at least substantially reduces the taste in restaurants, for example at airports or close to the road, because the gustatory nerves and the olfactory nerves are blocked to such an extent by the base load of stink that they are unable to perceive any shades. It is also known that the continuous presence in highly charged air renders tired and fatigued. Human beings, which have to work in bad air make after some time significantly more errors as compared to human beings, which work in problem-free air. It is also known that electrostatic charges are generated to an increased extent, if the air present in the room is poor in ions or, respectively, where positively charged ions or negatively charged ions dominate. Such air, commonly designated as "electrically charged" exerts uncontested influence on the vegetative nervous system. Furthermore, damages of electronic apparatus and data carriers can occur based on static charges. In addition, the level of sick people in enterprises, which are not able to offer good breathing air to their coworkers based on bad functioning air conditioning plants, is substantially higher as the level of sick people of enterprises, where attention is paid to perfect air.

The passengers in a motor vehicle are annoyed and at times damaged in their health based on the exhaust gases of other motor vehicles. The journal "Scientist", issue September 1996, cites in this context a Danish investigation, according to which the risk to become sick with lung cancer is for bus drivers 50 percent higher than in a comparison group of persons. Sensible known steps for reducing the emissions of passengers of motor vehicles are for example sensor controlled ventilation systems, wherein the inflow of outer air is stopped always then and switched to circulating operation, when the vehicle reaches a zone of increased contaminant concentration. Furthermore active carbon filters are known and are employed, which have a limited retaining capacity relative to some gases and vapors and of course dust and pollen. Larger concentrations however cannot be retained by the filters. In addition, there exist filter passing gases such as for example the poisonous carbon monoxide and finest dust and soot, such as are given off for example by diesel motors, which are considered to be cancer promoting.

In general the known ionization apparatuses are furnished with a hand operated switch, with the aid of which taps at transformers can be switched with the effect, that different voltages are fed to the ionization tube in order to be able to adjust in this fashion the power of ionization. Such an arrangement can operate substantially satisfactorily, if it is a purpose, for example to hold the number of germs small in a cold storage depot, because in general no substantially varying air contamination with other atmospheric pollutants occurs in a cold storage depot. However, the concentration of the air impurities varies substantially in nearly all other applications and possibly in a ratio of 1 to 10,000.

A fixedly set ionization apparatus cannot lead to a satisfactory solution in these cases, because either the ionization power is insufficient and thereby the smells and germs are not effectively combated or however in case of ionization powers set to a high level contaminant load appear interfering in case of a low air contamination by smellable and possibly dangerous ozone concentrations.

Technical Purpose

It is an object of the present invention to create an apparatus for the physical processing of air, in particular of breathing air, which corresponding to the load of the air with smelling materials or exhaust gases is capable to perform an ionization of the air depending on the concentration of the smelling materials or exhaust gases. One of the essential technical problems comprises, to adapt the ionization power of the recited ionization apparatus such that on the one hand an effective combating of smells and germs is furnished and on the other hand however, no excess ozone concentration should be generated thereby.

DISCLOSURE OF THE INVENTION AND ITS ADVANTAGES

The solution of this object comprises an apparatus of the initially recited kind, wherein the air ionizer is coupled to a sensor, which sensor determines the contents of the air in oxidizable gases (air quality sensor) and based on the determined contents of such oxidizable gases, the fed in electrical energy is changeable by way of an electric control device such that in case of low concentrations of oxidizable gases only a low ionization power is furnished, which can be increased controlled by a sensor and automatically with increasing concentration of oxidizable gases to a maximum value.

According to a further embodiment of the invention, an ion counter disposed after the air ionizer detects the number of the ions present in the air and acts through an electric circuit such onto the device or, respectively, the air ionizer, that in case of a low ion number the ionization power of the air ionizer is increased sensor controlled and automatic, and preferably continuously, and in case of a high ion number the ionization power of the air ionizer is decreased sensor controlled and automatic, and preferably continuously. Thus the control of the ionization power of the air ionizer is connected according to the gas load of the air, in particular of the breathing air.

The transformer exhibits various winding taps for changing the controlled power of the air ionizer and the transformer can be controlled through the winding taps such that, effect correctly and sensor controlled, a higher or lower operating voltage of the air ionizer results. In a similar way a chain of capacitive resistors or ohmic resistors can be switched in front of the air ionizer for changing the drive power of the air ionizer, wherein the chain of capacitive resistors or ohmic resistors is such bridged by suitable switching members of an appropriate effect, that an adapted, controlled ionization power of the air ionizer results according to the bridging. The appropriate effect and situation adapted change of the ionization power can also be achieved by having a plurality of air ionizers present and operating, wherein the active area of the operating air ionizers is adapted to the requirements determined by the air quality sensor or air quality sensors based on suitable electrical switching members. The increase of the ionization power occurs controlled by a sensor always then, when the change of the gas concentration detected by the air quality sensor exhibits a certain quotient over time. Or, the increase of the ionization power of the air ionizer can also then occur controlled by a sensor, where the gas depending value of the air quality sensor or the quotient from the value change of the air quality sensor over a time period exceeds a certain value.

According to a further embodiment the apparatus or, respectively the air ionizer is predisposed or integrated into an air humidifier.

An ozone sensor follows to the air ionizer for expanding the application spectrum, wherein the ozone sensor is connected to the electrical control circuit and wherein the ozone sensor acts onto the electrical control circuit upon determination of a certain ozone content in the air, wherein the electrical control circuit decreases the electrical energy fed to the air ionizer. A driving with a saw-tooth shaped voltage can be performed in case of an occurrence of ozone for controlling the electrical energy fed to the air ionizer, wherein the saw-tooth shaped voltage is reduced to such voltage upon reaching of a voltage permitting ozone production, at which voltage on the one hand a safe ionization occurs, but on the other hand however, still no ozonization occurs. This saw tooth shaped voltage can oscillate back and forth within a voltage band between the two voltage levels and can be formed like a ramp or formed like a saw tooth.

According to an advantageous embodiment the air ionizer comprises two or several electrically contacting planar or plate shaped structured bodies as electrodes, which are disposed in parallel planes and opposite to each other and which are electrically separated from each other by a dielectric and which form a planar capacitor, wherein a sufficiently high alternating voltage is applied to the electrodes for ionizing the air.

Furthermore, the air ionizer can comprise a planar outer electrode and a planar inner electrode, which are enclosed hermetically by a dielectric carrying the outer electrode, wherein the outer electrode and the inner electrode in each case are contacted by the electrical connection, and wherein an electrical alternating voltage sufficiently high for the ionization of air is connected to the inner electrode and to the outer electrode.

A plurality of flat air ionizers (flat ionizer) are stacked to a stack or to several stacks electrically isolated from each other, which stacks are passed through by the air to be treated, wherein a sufficiently high electrical alternating voltage is applied the individual electrodes for ionizing air. The inner electrodes can assume the same electrical potential as the neighboring flat ionizers or the inner electrodes can exhibit an electrical potential unequal to the neighboring flat ionizers.

According to an advantageous embodiment the air ionizer is permeable to air, wherein the two planar electrodes exhibit breakouts and are structured like a grid or like a hole, and wherein the air to be ionized flows through the free cross-section of the electrodes. One of the electrodes comprises an electrically conducting filtering material, which filtering material is grid like and electrically insulated surrounded by the other electrode; and the air to be treated flows through both electrodes.

At least one of the electrodes exhibits a plurality of needles or tips directed against the counter electrode in order to increase the corona effect.

A stack of ionization plates is disposed in a ventilation channel and fills the complete cross-section of the ventilation channel, and thereby forms and air ionizer, wherein the ionizer plates are aligned either with the narrow side front face, or with their cross-sectional face passable by the air toward the flow of air. Such an apparatus can be incorporated into an air channel transporting outside air of a motor vehicle.

SHORT DESIGNATION OF THE DRAWING

FIG. 1a is a schematic diagram of a side elevational view of a known air ionization apparatus, comprising a glass tube, wherein the inner wall of the glass tube and the outer wall of the glass tube are electrically covered with a wire grid and which forms a capacitor;

FIG. 1b is a schematic diagram of a sectional view of the embodiment of FIG. 1a;

Figure 3:
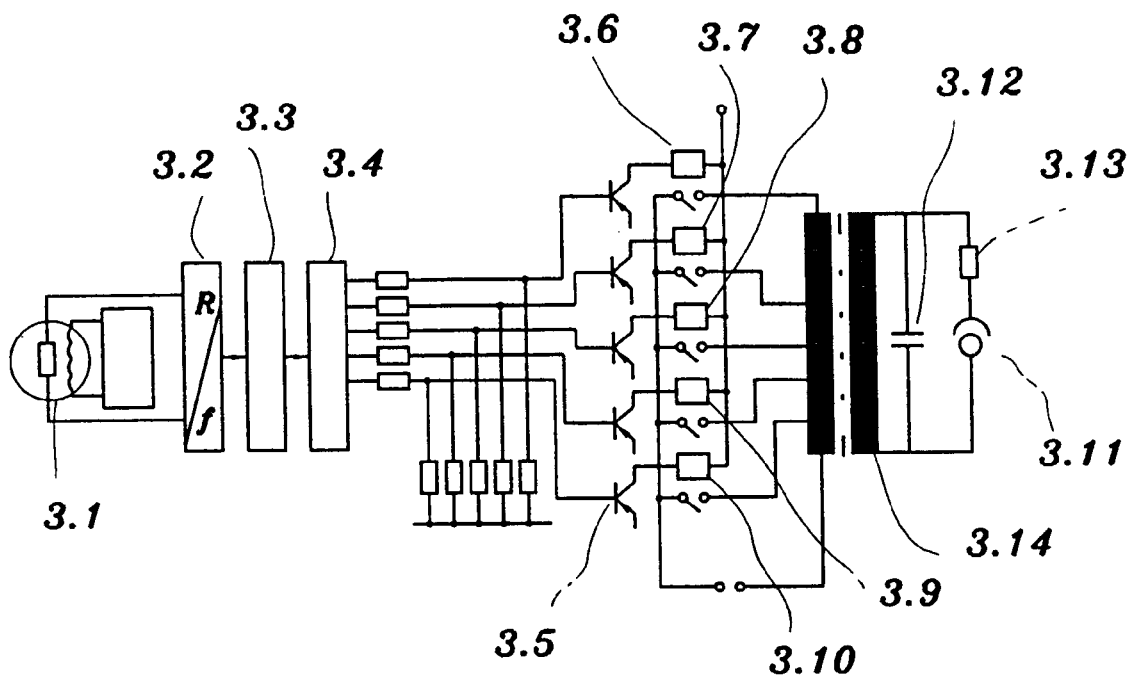
Figure 4:
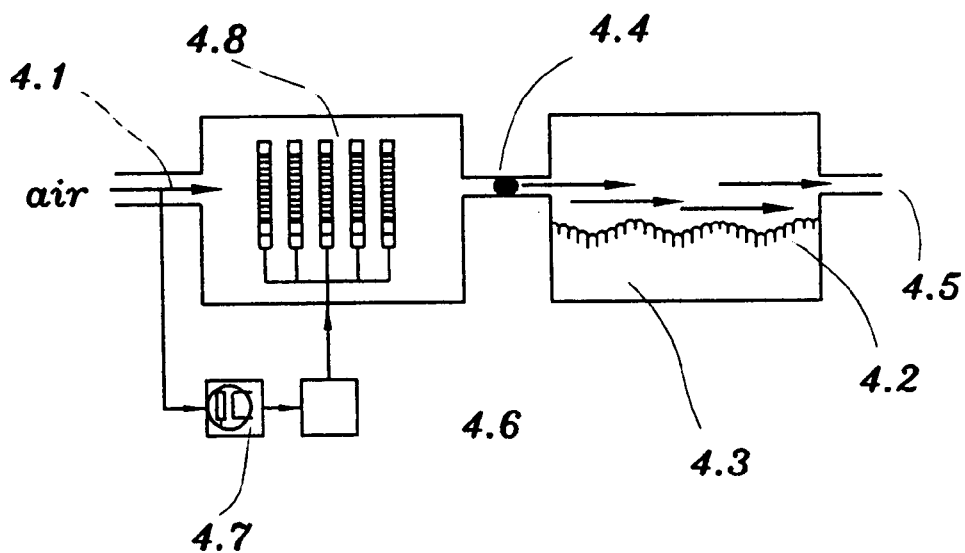
Figure 5:
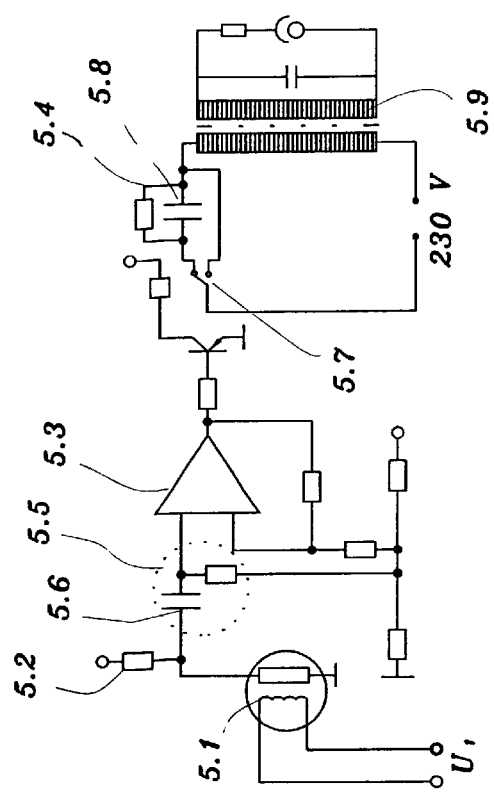
Figure 6:
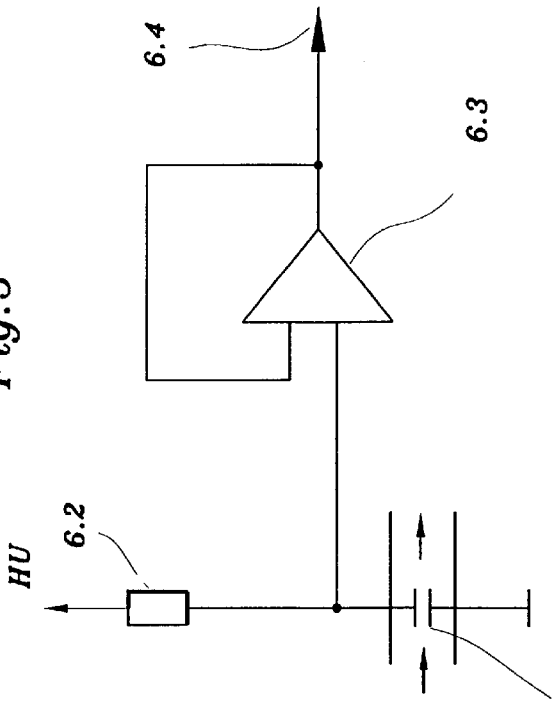
Figure 7:
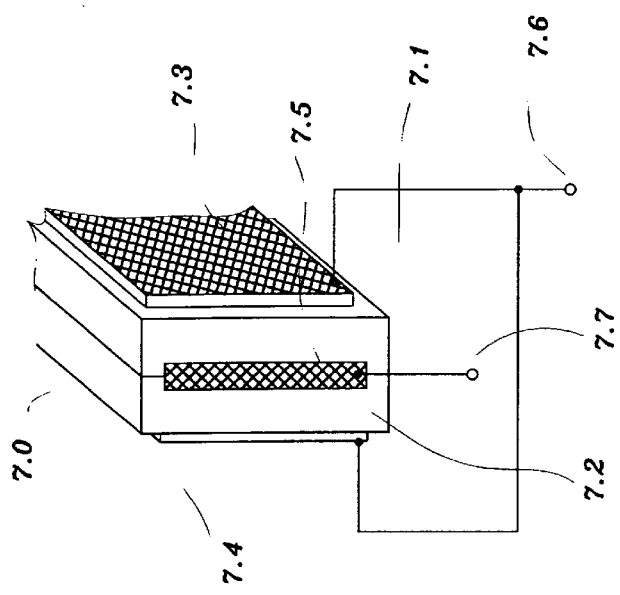
Figure 8:
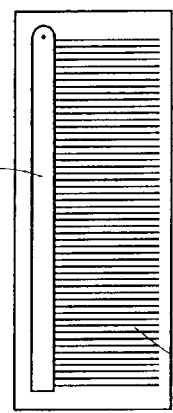
Figure 9:
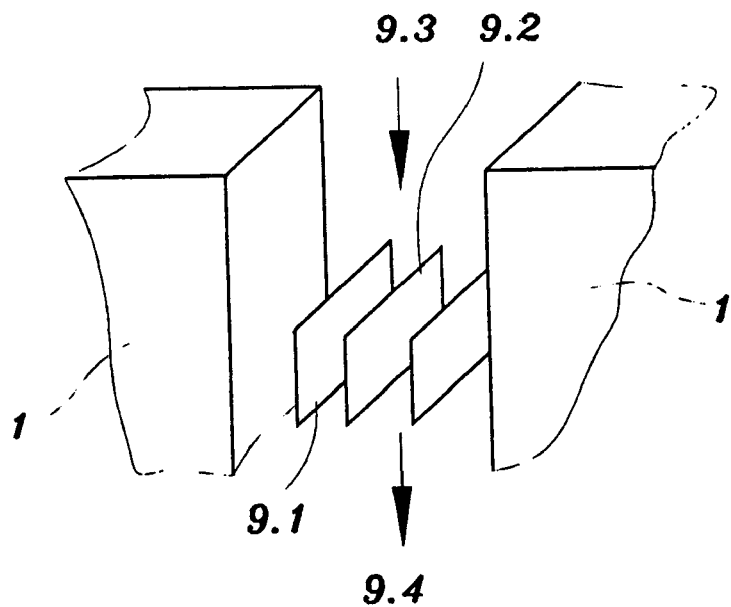
Figure 10:
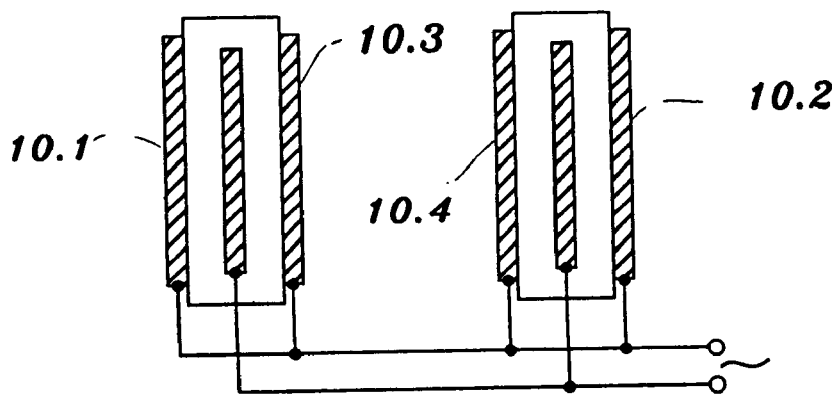
Figure 11:
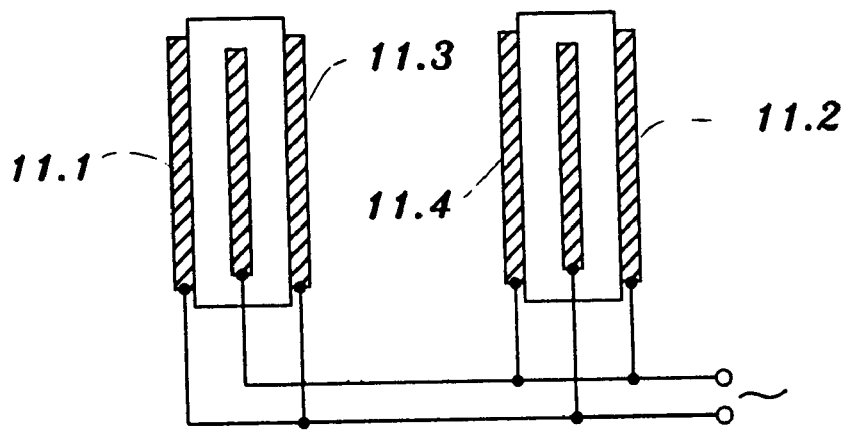
Figure 12:
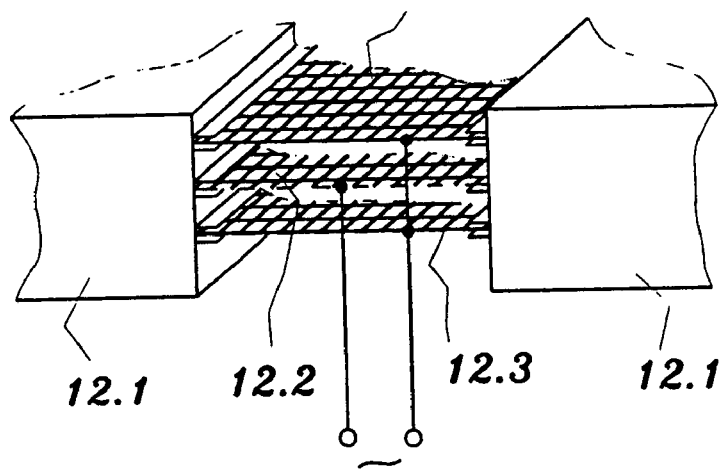
Figure 13:
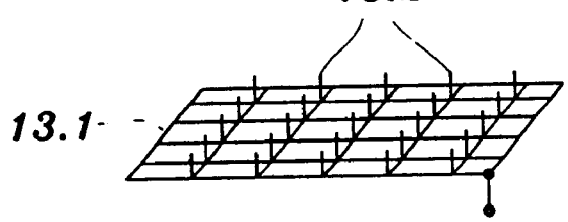
Figure 14:
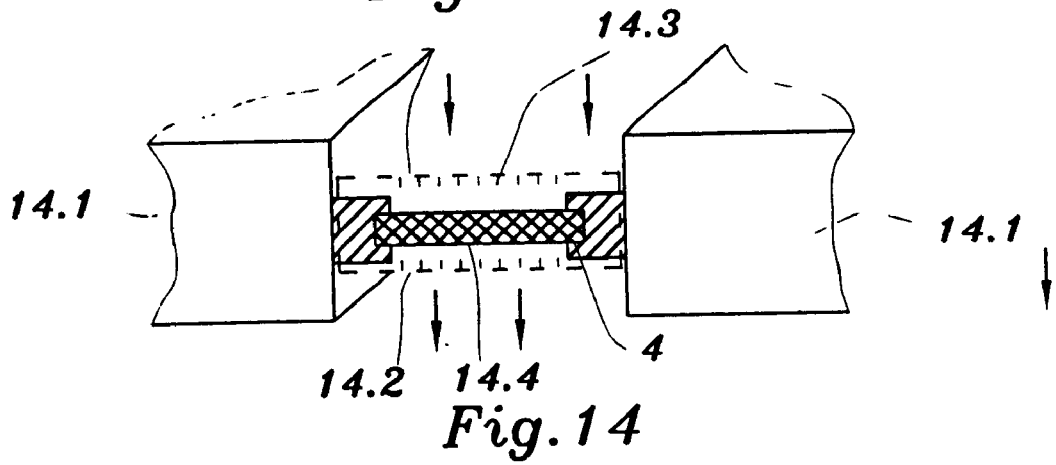
Figure 15:
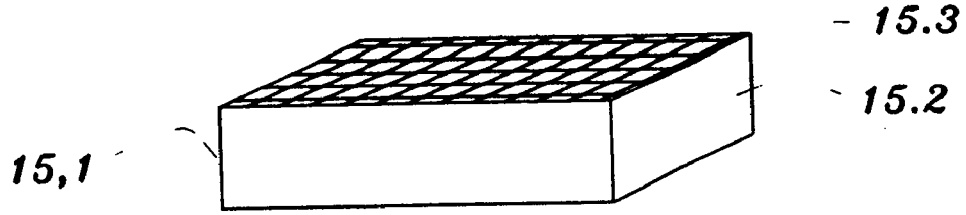
Figure 16:
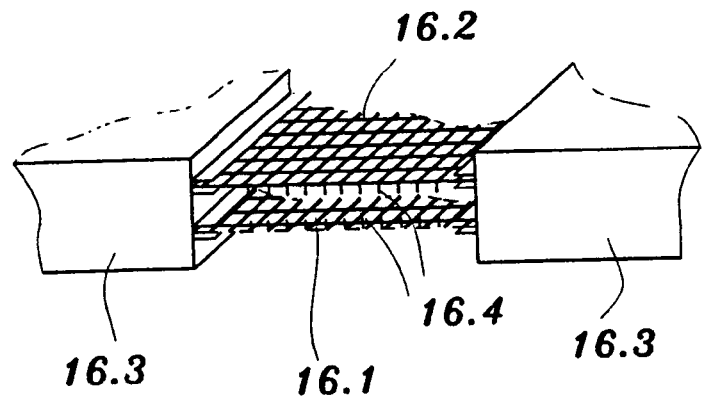
Figure 17:
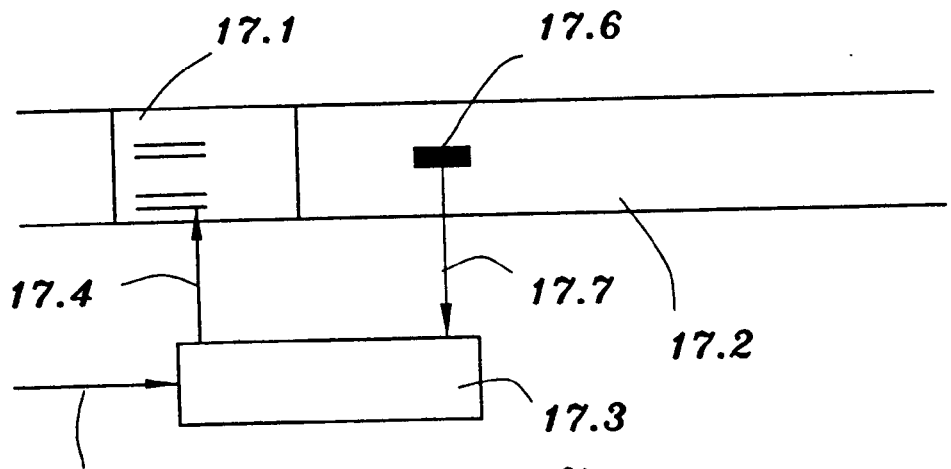
Figure 18:
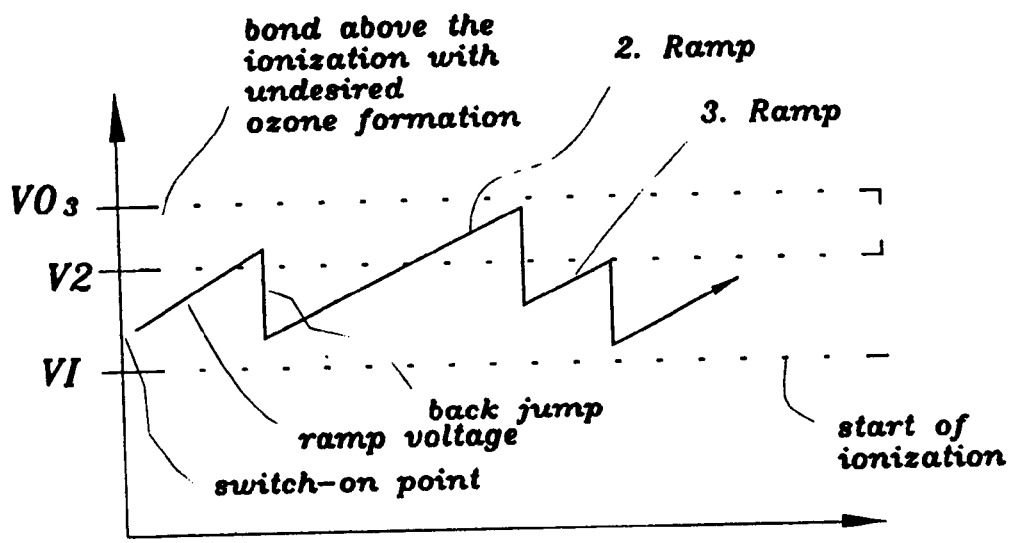
Figure 19:
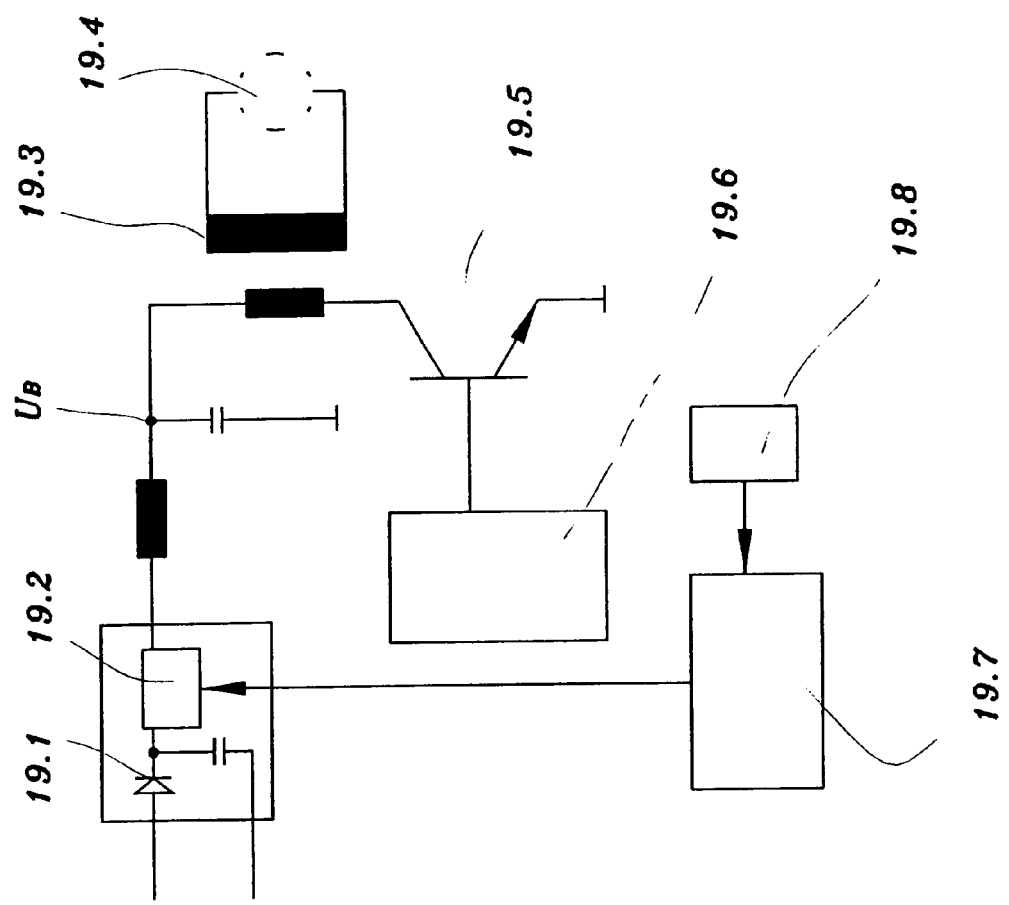

FIG. 2, a diagram of the contamination of the air with oxidizable pollutants to be detected by a metal oxide semiconductor sensor;

FIG. 3, a device according to the present invention for detecting the quality of the air;

FIG. 4, a device according to the present invention in combination with an air humidifier;

FIG. 5, a further device according to the present invention in an electrical circuit, which device increases the ionization power for a pre-determinable time period and then again reduces or switches off the ionization power;

FIG. 6, a circuit with an ion detector following to the air ionizer for controlling the air ionizer;

FIG. 7, an air ionizer in a flat construction form as a flat ionizer;

FIG. 8, an outer structure of the air ionizer of FIG. 7;

FIG. 9, a stack of plates out of a plurality of air ionizers (FIG. 7) according to the present invention, which air ionizers are disposed next to each other;

FIG. 10, a circuit variation of two flat ionizers according to FIG. 7;

FIG. 11, a further circuit variation of two flat ionizers according to FIG. 7;

FIG. 12, a flat ionizer or a plate ionizer wherein the electrodes are constructed grid like and air permeable and wherein the air flows through the free cross-section of the electrodes;

FIG. 13, an individual electrode of such a flat ionizer or plate ionizer according to FIG. 12;

FIG. 14, a further air ionizer, wherein the one, internal electrode passed by air comprises activated carbon FIG. 15, a perspective view of such an air ionizer according to FIGS. 12, 13 and 14, such as can be incorporated into the suction channel of a vehicle;

FIG. 16, a variation of such an air ionizer, wherein the electrodes exhibit needles or tips directed toward each other;

FIG. 17, an arrangement of an air ionizer in an air channel, wherein an ozone sensor for controlling the air ionizer is connected following the air ionizer, FIG. 18, a diagram of the ramp like voltage, which oscillates back and forth between two voltage values VI and VO3, and;

FIG. 19, a block circuit diagram of an electrical circuit for generating the ramp shaped voltage.

ROUTES FOR PERFORMING THE INVENTION

The FIGS. 1a and 1b show a known ionization apparatus for illustrative purposes, wherein the known ionization apparatus comprises essentially a glass tube 1.1, wherein the wall of the glass tube is electrically conductingly disposed on the inside and on the outside with in each case a wire cloth 1.2 or, respectively, 1.3. A high voltage is connected to the two wire grids insulated from each other, wherein the high voltage is generated by a transformer 1.4. Physically a capacitor is present, wherein the capacitance faces of the capacitor are formed by the two wire cloths 1.2 and 1.3 and wherein the glass wall 1.1 represents the dielectric. If an electric alternating voltage of, for example 3,000 volts from the transformer 1.4 is applied to the wire cloths 1.2 and 1.3, then a so-called "quiet discharge" occurs. Negative ions of oxygen clusters are generated at the surfaces of the wire cloths 1.2 and 1.3, this is the so-called active oxygen. At higher voltages also ozone (03) is necessarily generated, which ozone exhibits a stenching smell and which can be smelled already at concentrations of only about 50 ppb and which ozone can be damaging to health in higher concentrations from about 100 ppb. The fact that the active oxygen produced by ionization apparatuses oxidizes and thereby can render harmless the majority of the contaminations occurring in air with smelling materials, germs, bacteria and other pollutants, is known and had been proven in numerous scientific investigations. In addition, the unilateral charging of apparatuses or persons is avoided. These remarkable properties are based on the fact that the recited content materials of air are nearly throughout chemically oxidizable materials and in most cases of an organic nature.

Scientific investigations, for example in factories for foodstuffs, have shown that upon employing of ionization apparatuses, the number of germs per cubic meter was reduced from originally 800 to 1,000 to 30 to 60 on average and the propagation of germs was heavily inhibited. A practical test performed in an airport restaurant has shown that a present kerosene smell heavily criticized previously by guests and personnel could be reduced by the employment of ionization apparatuses in the air feed with such a success, that the kerosene smell could not any longer be perceived by test persons.

The invention is based on a sensor controlled control of an ionization apparatus for an air ionizer according to the diagram of FIG. 2. The y-axis 2.1 has plotted the detected contamination of the air with oxidizable pollutants, for example cigarette smoke, kerosene or industry waste gases or motor vehicle exhaust gases, solvent and alike with a metal oxide semiconductor sensor, for example according to the printed patent document WO 97/41423. The desired ionization power is plotted on the x-axis 2.2. It can be recognized that in case of very low air contaminations a constantly low ionization power can be set, in order to maintain the number of air ions, namely active oxygen ions, on a stable level, and thereby to counteract the subjectively recognizable "smell" of so-called "dead air" and in order to render the air in contrast "fresh". This is important because human beings in fact cannot smell active air ions, but can certainly determine the difference between the air coming from the outside and furnished with the high number of active air ions and "stagnant air" or "stale air" in closed interior rooms without parts of active air ions. In case of high air contaminations 2.3 the ionization power stagnates based on the in practical situations limited power of the ionization apparatuses. The ionization power 2.4 and 2.5 of the air contaminations according to the invention follows automatically and sensor controlled, preferably in a steady way between these points.

A sensor for detecting the air quality is illustrated in FIG. 3. A heated sensor element 3.1, namely for example a metal oxide semiconductor sensor according to the printed patent document WO 97/41423, operates like an electrical resistance, which electrical resistance assumes the value of about 40 kohm in case of un-contaminated air. If however oxidizable gases or vapors are present in the air then the electrical resistance drops to a value corresponding to the gas concentration of for example five kohm or less. The change in resistance is therefore a measure for the contamination of the air with pollutants. In a simple case the sensor 3.1 can be switched in series with an ohmic resistor such that a voltage divider results. Then the voltage change is a measure for the contamination of the air.

Furthermore it has been proposed to control of the ionization apparatus with pulse packets, wherein then the pulse pause ratio is controlled by the sensor. According to this method permanent ionizing occurs in case of heavily contaminated air. In case of slightly contaminated air a pulse packet of only short duration is generated, which pulse packet is followed by a comparatively larger pause. The pulse pause ratio is therefore a function of the quality of the air. In connection with the otherwise flawless functioning it is disadvantageous that the crackling or bubbling noises necessarily resulting during the ionization are acoustically so to say chopped, and with a result somewhat reminding of the noise of a cricket and usually perceived by persons to be very annoying.

It has been furthermore proposed to influence the power fed to the ionization apparatus based on the known method of the phase control such that a control possibility results running along a characteristic curve. This method proves in practical situations as being difficult to apply, because the inductive load to be controlled exhibits substantial tolerances and limits a flawless and reproduceable control of the ionization power. In addition, difficult to master electromagnetic radiations occur in connection with this kind of control, which radiations can only be suppressed with substantial anti-interference expenditures.

The circuit of the sensor shown in FIG. 3 takes the following path, wherein then the resistor of the sensor element 3.1 is incorporated into an electrical oscillator circuit 3.2 and forms part of this electrical oscillator circuit 3.2. A frequency of the oscillator circuit results, wherein the high level of the frequency of the oscillator circuit is a function of the sensor resistance. Typically a low frequency results in case of un-contaminated air, typically a clearly higher frequency results in case of contaminated air.

An electrical frequency counter 3.3 connected behind the oscillator circuit 3.2 determines the frequency and switches correspondingly its output contacts, which preferably deliver a binary coding of the momentarily furnished frequency. The signals are entered into an evaluation logic 3.4, which decodes the signals and thereby controls driver transistors 3.5 for certain frequency groups or frequency steps corresponding to the air quality/level, which driver transistors 3.5 switch successively connected relays 3.6, 3.7, 3.8, 3.9, and 3.10. The relays 3.6 to 3.10 in turn switch an electrical transformer 3.14 such that the generated secondary alternating voltage is stepped, for example between 1,500 and 3,200 volt, and is applied to an ionization tube or to an air ionizer 3.11. A combination of a capacitor 3.12 connected parallel to the secondary winding of the transformer 3.14 and a resistor 3.13 also connected parallel to the secondary winding of the transformer 3.14 serve for the suppressing of high frequency interfering pulses, which are generated based on the discharge processes in the ionization tube, in case such an ionization tube is employed.

Other practical circuits are conceivable, in particular analog circuits with a window discrimination coordinated to the ionization stages or complete digital solutions with a microprocessor. It is common to all circuits according to the present invention that the ionization power is automatically controlled by changing of the fed in electrical energy depending on an air quality sensor. Furthermore, the electrical or mechanical relays can be substituted by semiconductor switches, for example by Triacs without thereby going beyond the basic idea of the present invention.

It is thereby accomplished that always a sufficient and adapted ionization power of active ions is generated to such extent that an effective combating of odors, organic materials, bacteria and viruses is assured and that the static charging is substantially re-strained, which is of essential importance when employing the invention for example in an electrical production.

It is simultaneously assured that never annoyances or even endangerment of persons occur based on overshooting ionization powers, wherewith smellable ozone concentrations could be associated. Thus the effective and dangerless use of the advantageous ionization technique is always there possible, where dangerous or unpleasant air content materials or germs have to be combated and where an electrical flawless room climate is to prevent static charges.

Furthermore, the technology according to the present invention can be combined with known air treatment plants. For example, it is known to humidify air with apparatuses, wherein, for example a battery of rotatable disks immersed about half into water are passed by air. Here water is evaporated on the relatively large faces of the battery of disks, wherein simultaneously dust and some water-soluble air components are bound in the water. However, it is disadvantageous that germs are especially cultured in the humid medium of the wet plates and can reach substantial and dangerous concentrations in the water bath. In case of flowing over the plates, then germs can be dragged along during evaporation of the water and they can be enriched disadvantageously in the following in the breathing air.

For this purpose it is recommended to the users of such apparatuses to add sterilizing additives to the water bath, which generates additional costs and pains and is also biologically questionable, because also the additives are in part carried by the air and evaporate into the breathing air.

A combination of the apparatus according to FIG. 3 with a humidifying technique is the shown in FIG. 4. The air is led over one or several air ionizers 4.8 at the flow-in side 4.1 of the apparatus according to FIG. 4 for the air. The ionization power is controlled by an electrical control apparatus 4.6 depending on a gas sensor 4.7 for detecting oxidizable air components according to the statements made relating to FIG. 3.

Germs are reliably extinguished by the ionization and the thereby generated active oxygen ions and odors and gas shaped or vapor shaped oxidizable air components are oxidized and thereby rendered non-dangerous. A part of the active oxygen ions is bound in the water of a water bath 4.3 at the humidifying surface 4.2 and thus passes into the water bath 4.3 and is able there to combat germs present and prevent that the germs can further propagate. The air transport is assured by a ventilator 4.4. Air is made available at the blowout side 4.5 following to the water bath 4.3, wherein the quality of the air is substantially increased based on the arrangement according to the present invention. On the one hand the air is pleasantly humidified, and on the other hand the air is free from gaseous or vaporous pollutants or odorous materials and from germs.

A further field of applications includes ionization apparatuses for air refreshing in interior spaces with a limited ventilation, for example in toilets, showers and bathrooms or also in storage spaces and basements. In these cases one can operate with a small ionization apparatus permanently according to the present invention with a small power such that germs are extinguished and the air is always pleasantly fresh based on the presence of active oxygen ions.

If an enrichment of the air with gaseous materials occurs, for example in case of a use of a toilet or in case of releasing of odorous materials by new storage into a room, then this is detected by sensor 5.1 according to FIG. 5, and which sensor 5.1 operates as described in connection with FIG. 3, and the ionization power can be increased as required by a corresponding circuit as described in connection with FIG. 3. According to the present invention in this case the ionization power is increased only for a settable, limited time period, namely if the gas sensor detects an increase in the contamination of the air.

For this purpose the gas sensor 5.1 according to FIG. 5 is connected with an electric resistor 5.2 to a voltage divider. The electrical divider voltage resulting at the resistor 5.2 is then a function of the air quality. If the sensor element 5.1 becomes low ohmic based on an increasing contamination of the air, then the divider voltage at the resistor 5.2 changes according to the voltage divider rule. A successively connected capacitor 5.6 as a high pass filter 5.5 with adapted transfer frequency transfers only the voltage change and not static sensor level to a comparator 5.3, wherein the output pulse of the comparator 5.3 triggers a time function element 5.4. The output of the time function element 5.4 controls a switching relay 5.7. While usually a decrease of the ionization power is set by pre-connecting a capacitor 5.8 in front of the transformer 5.9, then when the air contamination increases by a predetermined amount, a higher ionization power is temporarily switched on with the switching relay 5.7 by driving the transform of 5.9 directly with the grid voltage.

The number of the negative ions present in air is determining for the electrical room climate. If the air in a room becomes "stale" or charged with particles, vapors or smoke, then the number of ions partially decreases to zero. When air is treated with electrical air ionizers as described above, then the number of ions increases and reaches the "usual level" present in fresh outside air.

In case of overdone ionization however the formation of smellable ozone occurs, which should be avoided.

Therefore it is provided according to the present invention to successively connect an ion detector to the air ionizer or to install the ion detector in the room to be ventilated. According to FIG. 6 such ion detector essentially comprises a plate capacitor 6.1 with the dielectric air. A certain amount of air is pressed by a small ventilator to the plates of the plate capacitor 6.1. The plates of the plate capacitor 6.1 are subjected to electrical charge, wherein an electrical voltage is applied to the plates 6.1 through a resistor 6.2. The ions generate a transport of charge and therefore a small current flow, which can be picked up at the resistor 6.2 and which is fed as an input signal to an impedance converter or impedance buffer 6.3 and which is output by the impedance converter 6.3 as a signal 6.4. For example the sensor of the arrangement according to FIG. 3 can be replaced with this signal.

According to the present invention the signal 6.4 representing the ionization can be employed as a control signal such that the ionization power of the apparatus is increased, if a low number of ions is present and wherein the ionization power is decreased, in case the desired number of ions has been reached or exceeded.

Thus the ion detectors according to FIG. 6 control the ionization power by the electrical influence according to one of the precedingly described methods according to the present invention; alternatively a control with a constant voltage is possible with controlled pulse pause ratios; also alternatively the control with a constant voltage is possible, wherein the energy feed in the individual alternating voltage cycles can be furnished with the so-called phase control.

A further possibility to change the ionization power comprises that the employed active face of the ionization apparatus is changed for example by changing the number of the employed ionization tubes or ionization apparatuses. Usually an arrangement with a plurality or multitude of air ionizers is employed in particular in large plants with substantial air capacity output. According to the present invention it is provided to employ one of the precedingly recited ionization apparatuses with a suitable controlled electronics such that number of the actively operated ionization apparatuses or air ionizers is changed depending on the desired ionization intensity. In general it can be added to this, that in case of a high air pollution or a high volume of air all ionization apparatuses are operated and in case of clean air only a single or no ionization apparatus is operated in order to avoid overshooting ion production and/or to avoid the danger of ozonizing.

It is an essential part of the invention to replace the tubular air ionizers, which are up to today in many cases employed and recited precedingly in FIG. 1, by other advantageous construction forms.

An air ionizer 7.0 according to the present invention is shown in FIG. 7, wherein the air ionizer 7.0 is distinguished by a more favorable ratio between volume and surface as compared to the known glass tube ionizers of the state of the art. Since the front faces are small, the flow resistance of the flat ionizers according to the present invention is substantially less as compared to conventional tubes. An inner electrically conductive face 7.5 is hermetically enclosed by two disks 7.1 and 7.2 or plates of electrically insulating material as far as the construction is concerned. Materials such as glass, ceramics, special plastics such as poly-tetra-fluoro-ethylene PTFE or similar materials are possible, which materials exhibit a high electrical breakdown strength and which materials forms a good dielectric. The disks 7.1 and 7.2 exhibit on the outside electrically conductive structures 7.3 and 7.4. Both in the internal electrical conducting face 7.5 as well as the outer structures 7.3 and 7.4 are contacted electrically conducting, wherein the feed to the structures 7.3 and 7.4 is formed by the feed line 7.6 and the electrical connection for the electrically conducting face 7.5 is formed by the feed line 7.7. The outer structures 7.3 and 7.4 and constructed with technologies such as silk screen printing, vapor deposition or etching or, respectively laser structuring such that a multitude of edges or tips are present and wherein high electrical superelevated field strengths occur at these edges or tips of the structure.

An example of such forming of the structures according to the structures 7.3 and 7.4 is illustrated in FIG. 8. Comb like or barbed wire like appendices 8.2 are applied at the conductor paths 8.1, which appendices 8.2 are not dissembling for example a barbed wire. Thus the structures can be produced in the recited sense, which serve for the generation of high field strengths at the edges and tips.

A high electrical alternating voltage is applied to the feed lines 7.6 and 7.7 in FIG. 7 during operation. The capacitor, which is finally concerned and which is disposed between the inner structure and the outer structure, is continuously reversely charged. The ionized gas molecules formed during the individual phases at the outer structures 7.3 and 7.4 are repelled during the next inversely poled phase and thus pass into the ambient air.

Stacks of plates according to FIG. 9 are constructed with the such a plate ionizer or flat ionizer according to FIG. 7. The individual plates 9.1,9.2, which correspond to the plate structure 7.0 of FIG. 7 are here disposed at the defined distance from each other and insulated from each other such that the air to be processed 9.3 flows through the plate stack 9.1,9.2 . . . and picks up a maximum of ions over the large face of the total stack of plates. The air 9.4 flowing out is enriched with oxygen ions. It is highly advantageous that the front face of the stack of plates of the plates 9.1,9.2 . . . is comparatively small relatively to the in flowing air 9.3 and that a relatively large ionization face is reached based on the plate face with a small volume.

Various switching variations are here possible for the plates 9.1,9.2 . . . , which are illustrated in the FIGS. 10 and 11. FIG. 10 illustrates two plate ionizers 10.1 and 10.2 according to FIG. 7, wherein the internal and the external faces in each case have the same electrical potential and are connected in this regard parallel, as can be gathered from FIG. 10. The advantage of this switching method comprises that the distances between the individual plates 10.1 and 10.2 can be selected to be very small, the each other facing in each case external faces 10.3 or, respectively 10.4 are under the same potential and thus no danger of an electrical sparking over exists. Thus an extremely large active ionization face can be accommodated in a little construction volume.

FIG. 11 shows two plate ionizers 11.1 and 11.2, wherein the internal faces and the external faces alternatingly exhibit changing potential relative to the neighboring plates and are connected antiparallel in this respect, wherein the distance between two neighboring outer faces 11.3 and 11.4 is selected such that no electrical spark-overs occur. The advantage of this circuit comprises that the air distance between the ionization plates or, respectively between the two outer faces 11.3 and 11.4 of two air ionizers 11.1 and 11.2 operates also as a dielectric and a substantial electrical field can be built up between the plates, which electrical field is capable to rip apart in particular polar molecules, such as for example hydrocarbon molecules. The combination of the influences "oxidizing with active oxygen ions" and "ripping apart of polar molecules in an electrical alternating field" allows to intensify the effect of ionization apparatuses.

FIG. 12 shows a further advantageous construction form of an air ionizer. Grid like, flat structures 12.2, 12.3, 12.4 are disposed inside of an insulated or, respectively insulating frame 12.1, which preferably forms a flow channel for the air fed through, wherein the grid like, flat structures 12.2, 12.3, 12.4 are planar, grid like bodies and exhibit electrically conducting surfaces. These bodies 12.2, 12.3, 12.4 are disposed planar parallel on top of each other in the air stream and are contacted electrically such that they exhibit in each case a changing electrical potential. The distances are selected such that no electrical spark-overs can occur. The material of the grid like flat bodies 12.2, 12.3, 12.4 can comprise wire fabric, punched metal parts or the like electrically conducting material.

The production rate of the ions according to the present invention is increased by a construction of electrically conducting flat bodies 13.1 by the situation that the electrically conducting flat bodies—or the flat bodies 12.2, 12.3, 12.4 in FIG. 12—are constructed similar to barbed wire and are provided with numerous needle shaped or tooth shaped projections 13.2, at which projections 13.2 the corona effect occurs particularly clear.

A further embodiment is shown in FIG. 14, wherein again an electrode 14.4 is disposed in an electrically insulating, and air channel forming, frame 14.1, which electrode 14.4 is insulatedly surrounded by cage 14.2. The inner electrode 14.4 is suspended electrically insulated from the outer electrode 14.2 and comprises an electrically conducting filter material of form pressed and foamed up active carbon. The guiding of the air is furnished such that the air flows through the outer electrode 14.2 and also permeates the electrically conducting filter material 14.25 by flowing through it. Air content materials as described are ripped apart in the electrical alternating field between the two electrodes 14.2 and 14.4 and simultaneously are oxidized by the active oxygen ions. Dusts and particles are retained in the active carbon mat 14.4. Pulse like occurring concentrations of gases or vapors are bound temporarily in the active carbon mat and are there oxidized by the active oxygen ions also flowing through the mat, so that the mat regenerates itself always and the feared desorption effects cannot occur. This construction can be repeated arbitrarily many times as a so-called "sandwich structure".

The outer, cage like electrode 14.2 can furthermore exhibit needle-shaped or tooth-shaped, electrically conducting tips 14.3 directed inwardly, wherein the corona effect occurs particularly clearly at the electrically conducting tips 14.3.

The ionization effect can be further increased, if a multitude of electrically contacted needles or tips are driven into the active carbon mat in order to reach the ion production intensifying corona effect relative to the counter electrode 14.2 or, respectively, the tips 14.3. Of course the recited needles can be formed also on the counter electrode similar to as is shown in FIG. 13 or they can be disposed alike on the two faces.

It is suggestive to employ a physical air treatment, as described, for treating the in-flowing air for vehicles. It is accomplished thereby that oxidizable gases such as gasoline vapors, kerosene odors or Diesel smells, poisonous carbon monoxide and uncombusted carbon, hydrogen, benzene and the like are oxidized and thereby rendered harmless. Such an air treatment apparatus for vehicles can be disposed in the neighborhood of the heat exchanger of the vehicle.

FIG. 15 shows such connection ready ionization module 15.1 in each case comprising an outer electrically insulating frame 15.2, which insulating frame 15.2 serves at the same time as a tube like air guide channel, wherein one surface of the frame 15.2 provides an inflow and where the treated air exits again at the other surface of the frame 15.2. Such planar electrode 15.3 as described previously in connection with FIGS. 7 through 14 are spanned and tensioned within the frame 15.2 over the cross-section face.

FIG. 16 shows a similar module, at which module here two electrically conducting planar air permeable plates 16.1 and 16.2 are supported within a frame 16.3. The two electrodes 16.1 and 16.2 comprise inwardly toward each other projecting needle shaped or tooth shaped tips 16.4, in order to increase the corona effect.

FIG. 17 illustrates a particularly advantageous method for the control of an air ionization unit, wherein the air ionization is performed either through a tube shaped or a plate shaped air ionizer 17.1, which air ionizer 17.1 is disposed in an air channel 17.2. The air ionizer 17.1 is furnished with voltage through a control electronic module 17.3 over the conductor line 17.4. The control electronic module 17.3 is connected to the power grid 17.5.

An ozone sensor 17.6 is disposed behind the air ionizer 17.1 in forward flow direction, where the ozone sensor 17.6 is capable to detect ozone possibly generated in the air ionizer 17.1. The ozone sensor 17.6 is connected to the control electronic module 17.3 through a line 17.7.

The mode of operation and functioning of the circuit according to FIG. 17 is explained in FIG. 18. It is known that the ionization function sets in at about a minimum voltage VI, the switch-on point. It is furthermore known that about a further voltage limit, namely the voltage VO3 the development of the undesired ozone occurs. This voltage limit is disposed higher with increasing air humidity and increasing air pollution as compared with dry and cleaned air. The voltage working range which is to be passed through by the air ionizer thus lies between the two voltages VI and VO3. Therefore a saw tooth shaped high-voltage of a frequency between 0.05 to 0.2 Hz is generated, which oscillates back and forth between the switch-on point above the start of the ionization VI and the voltage VO3 with the undesirable ozone formation. The high-voltage in the shape of a ramp voltage increases continuously by a fixed amount per time period after the switching on in the switch-on point. A production of ozone occurs above the voltage VO3, wherein the exact height level depends on parameters such as air stream, air humidity, air pollution and the like. The ozone sensor 17.6 recognizes this and conveys this to the control electronic module 17.3, which module reduces the high-voltage by a certain amount, namely the back jump in FIG. 18, which is disposed in that band, in which band ionization occurs, but in which band certainly no ozone production takes place. In the following the high-voltage is again increased and passes through the second ramp, until again an ozone formation occurs at the voltage point VO3 and again the high-voltage is reduced by a back jump from the second ramp. In the following this process can further be repeated. As a result the arrangement of the ionization plant runs such that the high-voltage is always disposed in a region, wherein on the one hand certainly ionization occurs, but on the other hand the region, wherein ozone formation takes place, is reliably avoided. Advantageously, the ionization voltage for the air ionizer 17.1 is always led such that the maximum ionization or also a desired ionization occurs without however permitting an overproduction of ozone.

A principal circuit diagram of electrical circuit is written in FIG. 19, showing how the function of the FIG. 18 can be electrically fulfilled. A pulse width voltage automatic controller 19.2 is integrated in a power grid rectifier 19.1, which pulse width voltage automatic controller 19.2 furnishes an operating voltage from about 50 to 150 volts for the primary coil of a high-voltage transformer 19.3 through an LC-member, wherein the secondary coil of the high-voltage transformer 19.3 is applied to an air ionizer 19.4. The primary coil is disposed in the collector-emitter circuit of a power transistor 19.5 for the pulse shaped high-voltage generation. A drive circuit 19.6, which controls the base section of the switching transistor, serves for switching transistor 19.5. The operating voltage flows through the primary coil of the high-voltage transformer 19.3 if the power transistor 19.5 is connected through. The control of the power transistor 19.5 is performed through the drive circuit 19.6 with a determined frequency and with a determined pulse pause ratio. According to a preferred embodiment a frequency of from 15 to 20 kHz is selected and a switching on ratio of 15 percent.

A control and automatic control unit 19.7 generates a saw tooth shaped voltage, which saw tooth shaped voltage influences the pulse width voltage controller 19.2 and which successively increases the output voltage of the pulse width voltage controller 19.2. An ozone sensor 19.8 is connected to the control and automatic control unit 19.7 and thus acts onto the control and automatic control unit 19.7 that upon occurrence of ozone the automatic control voltage and thus the high-voltage is reduced immediately to a measure which certainly does not any longer permit a production of ozone.

Commercial Applicability

The invention can be employed in particular commercially for the cleaning of air, in particular of breathing air. The usefulness of the invention comprises in particular that the air ionizer is capable to produce always an optimum of oxygen ions, without however thereby producing ozone.

What is claimed is:

1. An apparatus for generating active oxygen ions comprising
    an electrical transformer generating an electrical high-voltage sufficient for air ionization;
    an air ionizer connected to the electrical transformer;
    a sensor for determining the content of oxidizable gases in the air; and
    an electrical control unit connected to the electrical transformer, to the air ionizer, and to the sensor, which electronic control unit changes the electrical energy fed in to the air ionizer based on the content of oxidizable gases in the air as determined by the sensor such that in case of a low concentrations of oxidizable gases present in the air then only a small ionization power is effected, wherein the ionization power of the air ionizer increases to a maximum value as automatically controlled by the sensor and the control unit when an increase in concentration of oxidizable gases is sensed by the sensor.

2. The apparatus according to claim 1, wherein the sensor is an ion counter;
    wherein the ion counter is disposed following to the air ionizer and detects the number of ions present in the air and operates through an electronic control unit in such a way on the air ionizer that, in case of a presence of a small ion number in the air as sensed by the sensor, then the ionization power of the air ionizer is increased and, in case of a large ion number in the air as sensed by the sensor, then the ionization power of the ionizer is decreased automatically and continuously.

3. The apparatus according to claim 1 further comprising
    a plurality of winding taps disposed at the electrical transformer for changing the drive power of the air ionizer and wherein the electrical transformer is controllable through a connection to the winding taps such that a higher or lower operating voltage of the air ionizer results in the proper direction, wherein the connection to the winding taps is controlled by the sensor.

4. The apparatus according to claim 1 further comprising
    a chain of capacitors or ohmic resistors is preconnected to the air ionizer for changing the driver power of the air ionizer;
    switching members, wherein the capacitive or ohmic resistors are bridged for an appropriate effect through the switching members such that an adapted ionization power of the air ionizer results corresponding to the bridging.

5. The apparatus according to claim 1 further comprising
    a second ionizer connected to the control unit for allowing for a quicker change of the ionization power showing an appropriate effect and adapted to the situation and adapting the active area of the operating air ionizers to the requirement as determined by the air quality sensor.

6. The apparatus according to claim 4, wherein the increase of the ionization power as controlled by the sensor occurs when the level of the ion concentration detected by the air quality sensor falls below a certain quotient over a predetermined time period.

7. The apparatus according to claim 1, wherein an increase of the ionization power of the air ionizer is controlled by the sensor and occurs in each case then, when the gas dependent value of the air quality sensor or the quotient from the value change of the air quality sensor over a time period exceeds a certain value.

8. The apparatus according to claim 1 further comprising
    an air humidifier predisposed to the air ionizer.

9. The apparatus according to claim 1 further comprising
    an ozone sensor successively disposed to the air ionizer, wherein the ozone sensor is connected to the electrical control unit and wherein the ozone sensor, in case of determination of a certain ozone contents in the air, actuates the electrical control unit such that the electrical control unit decreases the electrical energy fed to the air ionizer when actuated by the ozone sensor.

10. The apparatus according to claim 9 further comprising
    a saw-tooth voltage generator connected to the electrical control unit, wherein the saw tooth generator delivers a driving saw tooth shaped voltage for controlling the electrical energy fed to the air ionizer in case of an occurrence of ozone, wherein upon reaching of a voltage permitting the production of ozone a reduction in such a voltage occurs, at which reduced voltage on the one hand safe ionization is performed, and on the other hand still no ozonization occurs.

11. The apparatus according to claim 10, wherein the saw tooth shaped voltage oscillates back and forth within a voltage band between two voltage levels shaped as a ramp or shaped as a saw tooth.

12. The apparatus according to claim 1, wherein the air ionizer comprises two electrically conducting, planar plate shaped structural bodies as electrodes, which electrodes are disposed opposing each other in a planar parallel relative position and which electrodes are electrically separated from each other by a dielectric and form a planar capacitor, wherein a high alternating voltage is applied to the electrodes, which high alternating voltage is sufficient for ionization of air.

13. The apparatus according to claim 1, wherein the air ionizer comprises a planar outer electrode and a planar inner electrode, which inner electrode is hermetically enclosed by a dielectric carrying the outer electrode, wherein the outer electrode and the inner electrode in each case are contacted by an electric connection, and wherein a high electrical alternating voltage sufficient for an ionization of air is connected to the inner electrode and to the outer electrode.

14. The apparatus according to claim 13, wherein a plurality of flat air ionizers are stacked to a stack of flat air ionizers electrically insulated from each other, which stack is passed through by the air to be treated and wherein a high electrical alternating current sufficient for an ionization of air is applied to the individual electrodes.

15. The apparatus according to claim 12, wherein the air ionizer is air permeable, wherein the two planar electrodes exhibit breakouts and are structured in the shape of a grid or in the shape of a hole and wherein the air to be ionized flows through the free cross-section of the electrodes.

16. The apparatus according to claim 15, wherein one of the two electrodes comprises an electrically conducting filtering material, which filtering material is surrounded by the other electrode in the shape of a grid, but electrically insulated, and wherein air to be treated flows through the two electrodes.

17. The apparatus according to claim 12, wherein at least one of the electrodes exhibits a multitude of needles or tips or teeth directed against the counter electrode.

18. The apparatus according to claim 12, wherein a stack of ionization plates is disposed in a ventilation channel, and fills the complete cross-section of the ventilation channel and in this way forms an air ionizer and wherein the ionization plates are aligned against the air flow either with the narrow side front face or with their cross-sectional face capable of permitting air flow.

19. The apparatus according to claim further comprising an air channel surrounding the air ionizer for incorporating the apparatus into a motor vehicle for transporting outside air.

20. The apparatus according to claim 1, wherein the ionizer is formed of grid-shaped, flat structures, wherein the grid-shaped, flat structures are disposed inside of an insulating frame forming a flow channel for the air fed through, wherein the grid-shaped, flat structures are planar, grid-shaped bodies and exhibit electrically conducting surfaces;
   wherein the planar, grid-shaped bodies are disposed planar parallel on top of each other in the air stream and are contacted electrically such that the planar, grid-shaped bodies exhibit in each case a changing electrical potential;
   wherein the distances between the planar, grid-shaped bodies are selected such that no electrical spark-overs can occur;
   wherein the material of the planar grid-shaped flat bodies comprises a member selected from the group consisting of wire fabric, punched metal parts, electrically conducting material, or combinations thereof.

21. The apparatus according to claim 20, wherein the planar, grid-shaped bodies are constructed as a barbed wire and are provided with a plurality of projections selected from the group consisting of needle shaped projection, tooth shaped projection and combinations thereof, wherein the projections are constructed to furnish a clear corona effect for increasing the production rate of the ions.

22. An apparatus for generating active oxygen ions in the air for breathing air, comprising at least one air ionizer and an electrical transformer generating an electrical high-voltage sufficient for air ionization, with a sensor determining the content of oxidizable gases in the air and an electrical control unit, which electrical control unit changes the electrical energy fed in to the air ionizer based on the determined content of oxidizable gases such that in case of low concentrations of oxidizable gases only a small ionization power is effected, which ionization power is increasable, as controlled by a sensor and automatically, with an increasing concentration of oxidizable gases to a maximum value.

23. Apparatus according to claim 22 wherein an ion counter is disposed following to the air ionizer and detects the number of ions present in the air and operates through an electronic circuit in such a way on the apparatus or, respectively, the air ionizer that, in case of a small ion number, the ionization power of the air ionizer is increased and, in case of an increased ion number, the ionization power of the ionizer is decreased, as controlled by a sensor and automatically;
   wherein the transformer exhibits various winding taps for changing drive power of the air ionizer and wherein the transformer is controllable through the winding taps such that a higher or lower operating voltage of the air ionizer results in the proper direction and is controlled by a sensor;
   wherein a chain of capacitors or ohmic resistors is preconnected to the air ionizer for changing the driver power of the air ionizer, wherein the capacitive or ohmic resistors are bridged for an appropriate effect through suitable switching members such that an adapted ionization power of the air ionizer results corresponding to the bridging;
   wherein a change of the ionization power is accomplished giving an appropriate effect and adapted to the situation, by employing and operating a multitude of air ionizers and adapting the active area of the operating air ionizers to the requirement as determined by one or, respectively, several air quality sensors with suitable electrical switching circuits;
   wherein the increase of the ionization power as controlled by a sensor occurs in each case then, when the change of the gas concentration detected by the air quality sensor exhibits a certain quotient over a time period.

24. The apparatus according to claim 23, wherein an increase of the ionization power of the air ionizer is controlled by a sensor and occurs in each case then, when the gas dependent value of the air quality sensor or the quotient from the value change of the air quality sensor over a time period exceeds a certain value;
   wherein an air humidifier is preconnected-connected to the air ionizer;
   wherein an ozone sensor is successively connected to the air ionizer, which ozone sensor is connected to the electrical control circuit and which ozone sensor, in case of determination of a certain ozone contents in the air, actuates the electrical control circuit, wherein the electrical control circuit decreases the electrical energy fed to the air ionizer;
   wherein a driving saw tooth shaped voltage is employed for controlling the electrical energy fed to the air ionizer in case of an occurrence of ozone, wherein upon reaching of a voltage permitting the production of ozone a reduction in such a voltage occurs, at which voltage on the one hand safe ionization is performed, and on the other hand still no ozonization occurs;
   wherein the saw tooth shaped voltage oscillates back and forth within a voltage band between the two voltage levels in the shape of a ramp or like a saw tooth.

25. The apparatus according to claim 22, wherein the air ionizer comprises two or several electrically conducting, planar or plate shaped structural bodies as electrodes, which electrodes are disposed opposing each other in a planar parallel relative position and which electrodes are electrically separated from each other by a dielectric and form a planar capacitor, wherein a high alternating voltage is applied to the electrodes, which high alternating voltage is sufficient for ionization of air;

wherein the air ionizer comprises a planar outer electrode and a planar inner electrode, which inner electrode is hermetically enclosed by a dielectric carrying the outer electrode, wherein the outer electrode and the inner electrode in each case are contacted by an electric connection, and wherein a high electrical alternating voltage sufficient for an ionization of air is connected to the inner electrode and to the outer electrode;

wherein a plurality of flat air ionizers are stacked to a stack or to a plurality of stacks electrically insulated from each other, which stack or stacks are passed through by the air to be treated and wherein a high electrical alternating current sufficient for an ionization of air is applied to the individual electrodes;

wherein the inner electrodes are subjected to the same electrical potential as the neighboring flat ionizers or the inner electrodes are subjected to an unequal electrical potential as compared to the potential of the neighboring flat ionizers;

wherein the air ionizer is air permeable, wherein the two planar electrodes exhibit breakouts and have grid-shaped or hole-shaped structures and wherein the air to be ionized flows through the free cross-section of the electrodes;

wherein one of the two electrodes comprises an electrically conducting filtering material, which filtering material is surrounded by the other electrode in the shape of a grid, but electrically insulated, and wherein air to be treated flows through the two electrodes;

wherein at least one of the electrodes exhibits a multitude of needles or tips or teeth directed against the counter electrode;

wherein a stack of ionization plates is disposed in a ventilation channel, and fills the complete cross-section of the ventilation channel and in this way forms an air ionizer and wherein the ionization plates are aligned against the air flow either with the narrow side front face or with their cross-sectional face capable of permitting air flow.

26. A method for improving the quality of air comprising generating an electrical high-voltage sufficient for air ionization;

applying the voltage to an air ionizer;

passing a stream of air through the air ionizer;

generating active oxygen ions in the stream of air passing through the air ionizer;

sensing the content of oxidizable gases in the air;

changing the electrical high voltage applied to the air ionizer based on the contents of oxidizable gases in the air as determined by sensing.

27. The method for improving the quality of air according to claim 26 further comprising changing the electrical high voltage applied to the air ionizer such that in case of a low concentrations of oxidizable gases present in the air then only a relatively small number of active oxygen ions is generated in the stream of air, and such that in case of a high concentrations of oxidizable gases present in the air then a relatively large number of active oxygen ions is generated in the stream of air.

28. The method for improving the quality of air according to claim 26 further comprising increasing the ionization power of the air ionizer as controlled by the sensor and occurring when the gas dependent value of an air quality sensor or the quotient from the value change of the air quality sensor over a time period exceeds a certain value;

observing a certain ozone contents in the air by an ozone sensor;

decreasing an electrical energy fed to the air ionizer when the certain ozone contents is observed by the ozone sensor;

generating a driving saw tooth shaped voltage for controlling the electrical energy fed to the air ionizer in case of an occurrence of ozone;

oscillating the saw tooth shaped voltage back and forth within a voltage band between two voltage levels in the shape of or a saw tooth;

reducing the voltage upon a reaching of a voltage permitting the production of ozone and wherein at which reduced voltage a safe ionization is performed, but still no ozonization occurs.

\* \* \* \* \*